United States Patent [19]

Vikmon et al.

[11] Patent Number: 5,298,496

[45] Date of Patent: Mar. 29, 1994

[54] INCLUSION COMPLEXES OF 3-MORPHOLINO-SYDNONIMINE OR ITS SALTS OR ITS TAUTOMER ISOMER, PROCESS FOR THE PREPARATION THEREOF, AND PHARMACEUTICAL COMPOSITIONS CONTAINING THE SAME

[75] Inventors: Maária Vikmon; József Szejtli; Lajos Szente; József Gaál; István Hermecz; Agnes Horváth, all of Budapest; Katalin Mármarosi, Biatorbágy; Gábor Horváth; Irén Munkácsi, both of Budapest, all of Hungary

[73] Assignee: Chinoin Gyogyszer- ES Vegyeszeti Termekek Gyara Rt., Budapest, Hungary

[21] Appl. No.: 793,389

[22] PCT Filed: Mar. 28, 1991

[86] PCT No.: PCT/HU91/00013

§ 371 Date: Jan. 2, 1992

§ 102(e) Date: Jan. 2, 1992

[30] Foreign Application Priority Data

Mar. 28, 1990 [HU] Hungary .................... 1869/90
Jun. 27, 1990 [HU] Hungary ............. 1869/90/MODIFI

[51] Int. Cl.⁵ ................ C07D 271/04; C07D 295/30; A61K 31/41; C08B 37/16

[52] U.S. Cl. ........................ 514/58; 536/103; 424/464; 424/499; 514/821; 514/969

[58] Field of Search .............. 514/58, 821, 969; 536/103; 424/464, 499

[56] References Cited

U.S. PATENT DOCUMENTS

| | | | |
|---|---|---|---|
| 4,786,507 | 11/1988 | Schmidt | 424/472 |
| 4,834,985 | 5/1989 | Elger et al. | 424/488 |
| 4,869,904 | 9/1989 | Uekama et al. | 424/489 |
| 5,120,546 | 6/1992 | Hansen et al. | 424/449 |

*Primary Examiner*—Ronald W. Griffin
*Attorney, Agent, or Firm*—Herbert Dubno; Jonathan Myers

[57] ABSTRACT

The invention relates to inclusion complexes of 3-morpholino-sydnonimine or its salts or its tautomer isomer, process for the preparation thereof and pharmaceutical compositions containing the same.

The inclusion complex of 3-morpholino-sydnonimine or its salt formed with cyclodextrin derivative is prepared by a) reacting the 3-morpholino-sydnonimine or its salt in an aqueous medium with a cyclodextrin derivative and the complex is isolated from the solution by dehydratation, or b) high energy milling of 3-morpholino-sydnonimine or its salt and a cyclodextrin derivative.

17 Claims, No Drawings

INCLUSION COMPLEXES OF 3-MORPHOLINO-SYDNONIMINE OR ITS SALTS OR ITS TAUTOMER ISOMER, PROCESS FOR THE PREPARATION THEREOF, AND PHARMACEUTICAL COMPOSITIONS CONTAINING THE SAME

CROSS REFERENCE TO RELATED APPLICATIONS

This application is a National Phase of PCT/HU91/00013 filed Mar. 28, 1991 and based upon Hungarian national application 1869/90 of Mar. 28, 1990 (amended Jun. 27, 1990) under the International Convention.

1. Field of the Invention

The invention relates to the inclusion complexes of 3-morpholino-sydnonimine (SIN-1) or its salts or its open ring "A" form tautomer (SIN-1A: N-nitroso-N-morpholino-amino-acetonitrile) formed with cyclodextrin derivatives, to the process of preparation and to pharmaceutical compositions containing them as active ingredients. The open ring "A" form plays an important role, its formation is predominant for NO (nitric oxide) radical liberation.

2. Background of the Invention

Molsidomin (N-ethoxycarbonyl-3-morpholino-sydnonimine, SIN-10) is a well-known antianginal agent. In therapy it is widely used for the treatment and prevention of angina in the case of heart insufficiency, in the state of heart infarct. The therapeutic effect of Molsidomin can be attributed mainly to its first active metabolite to the 3-morpholino-sydnonimine, which originates mainly in the liver by enzymatic hydrolysis and by subsequent effect of the decarboxylase enzyme. Thus the SIN-1 possesses a therapeutic advantage too compared to Molsidomin, that is its efficacy is quicker and more definite. Its disadvantage is that it can be used only in the form of intravenous injections.

The sydnonimine derivatives are extremely light-sensitive. Upon to irradiation with artificial or natural light for only a short time they will be decomposed quickly. In the course of photolysis pharmacologically inactive, but harmless decomposition products as e.g. morpholine, ammonia, ethyl alcohol, carbondioxyde form. The aim of some patents is the photostabilization of sydnonimine derivatives by the addition of different additives. (European Patent Specification No. 206219 and GFR Patent Specification No. 3.346.638).

The light-sensitivity can fairly be avoided in dry state and in solution by suitable storage (in a well-closed dark flask wrapped with black paper).

It can be generally said that the sydnonimine derivatives are sensitive to extreme pH values, and are decomposed quickly. The final product of the chemical and metabolitic decomposition of Molsidomin is the SIN 1C (cyanomethylene-amino-morpholine), an inactive metabolite. In the use of SIN 1 as a medicament the problems of chemical stability are coming to the fore. The substance decomposes quickly in a neutral-aqueous solution, it is sensitive to the pH value and it is stable only in a strong acidic medium (pH 1-2). Above pH 2 it decomposes quickly, to the inactive metabolite SIN 1C, that is connected with the loss of therapeutic activity. The SIN 1→SIN 1C transformation is the result of base catalyzed hydrolytic decomposition. The process is strictly pH dependent, e.g. to achieve a decomposition of 10% (SIN 1C) 53 sec. at a pH value of 8, 15 hours at a pH of 6, 67 days at a pH of 4, and 13 years at a pH of 1-2 are necessary. (Chem. Pharm. Bull. 19/6 1079, 1971). SIN 1 is also decomposed in a diluted aqueous solution stored in diffused lighting in 1-3 days. The decomposition can be followed from the UV spectrum directly. The value of the absorption maximum is shifted gradually from $291\pm1$ nm to $278\pm1$ while the value of absorption increases continuously, which is in harmony with the data of the literature: the $\lambda$ max. value of SIN 1 is $291\pm1$ nm, the specific absorption coefficient $A^{1\%}_{1 cm}=520$, while the SIN 1C $\lambda$ max. is $278\pm1$ nm, its molar absorption coefficient $\epsilon=17000$ $A^{1\%}_{1 cm}=1220$.

SIN 1 applied orally is not effective; between pH 1-2 SIN 1 has presumably a strongly ionized state of favourable chemical stability, which on the other hand is not favorable to the resorption from the G1 tract. Moving along from the stomach at a more basic pH in the sense of the above mentioned facts SIN 1 is transformed quickly into the inactive SIN 1C metabolite. The low dose of the SIN 1 applied is favorable to this transformation as the hydrolytic decomposition in low concentrations (of $\mu$/ml order) is still more definite.

SIN 1 is on the market in the form of its hydrochloride salt, for intravenous application in the form of a lyophilized powder ampoule containing 2 mg active ingredient and 40 mg of sorbite. The content of the ampoule has to be dissolved in 1 ml of distilled water before use.

OBJECT OF THE INVENTION

The object of the invention was to prepare such a new agent, by means of which the SIN 1→SIN 1C transformation can be hindered even in a neutral-aqueous solution, and at a physiological pH value.

DESCRIPTION OF INVENTION

It is known that the complexation with cyclodextrin is suitable to the stabilization of different agents against heat, light and basic or acidic hydrolysis. (Szejtli: Cyclodextrin Technology, Kluwer, Dordrecht, 1988., pages 211-217).

In the course of our investigations we have found, that the cyclodextrins have proved themselves effective to stabilize the dilute-aqueous solutions obtained from the SIN 1 injectable composition.

The interaction between SIN 1 and the cyclodextrins was proved by the following test series:

From the injectable SIN 1 composition we prepared an aqueous solution of about 10 $\mu$g/ml and in the solutions 20-40 mg of cyclodextrin or cyclodextrin derivative were dissolved while stirring.

The solutions were stored at room temperature (20°-22° C.) in diffuse lighting and in certain periods (daily) the UV spectrum of the solutions were registered in the interval between 220-350 nm. As a control only the aqueous solution, and the 0,05N hydrochloric acid solution were used respectively. The pH value of the cyclodextrin solutions were checked to determine, that cyclodextrin, and the derivative used, respectively, do not change significantly the pH value of water. The pH values of the applied cyclodextrin solutions of greatest concentration differed only within $\pm0.2$ unit from the pH value of distilled water. We found that the shift of the UV spectrum was conspicuously well hindered by CDPSI, an ionic soluble $\beta$-cyclodextrin polymer (average molecule mass 3500, β-CO content 54%, COO− content: 4.2%) (Hungarian Patent Specification No. 191.101). The shift of the spectrum was not experienced even after 2 weeks of storage, while the aqueous solution stored similarly was practically transformed into SIN 1C within 2-3 days.

The decomposition hindering, slow down effect of DIMEB (2,6-di-O-methyl-β-cyclodextrin) is definite too. In the presence of 20 mg/ml DIMEB the spectrum of the solution has shown only a shift within 1 nm after a 6 day storage. We also tested the stabilizing effect of TRIMEB (2,3,6-tri-O-methyl-β-cyclodextrin), of γ-CO, β-CO and of hydroxypropyl-β-CO. The efficiency sequence concluded from the UV spectrum shift was as follows:

CDPSI>DIMEB>TRIMEB>βCO≧HPβCO.

From the effect exerted on the hydrolytic decomposition of SIN 1 by the different cyclodextrins and outstandingly by CDPSI a complex interaction can concluded.

In the above test series the cyclodextrins and their derivatives were used in an extremely great excess (10 μg/ml of SIN 1 vs ~20 mg/ml of cyclodextrin).

The test series were repeated so, that CDPSI was applied used in a 10 fold or 20 fold excess, which corresponds to a SIN 1: CDPSI weight proportion in a complex containing 10% or 5% respectively of the active ingredient. The low therapeutic dose of SIN 1 allows even the application of a complex containing less than 5% of the active ingredient, which corresponds to a molar ratio of about 1:2 SIN 1: CDPSI. In such a concentration range spectrophotometric measurement dose not give a descriptive picture. For this reason the decomposition degree was determined by thin-layer chromatography in the following way: From the solutions 10 μl were dropwise added on a Kieselgel 60 $F_{254}$ plate (10×10 cm, Merck). Running mixture: cyclohexane:ethyl-acetate in a ratio of 1:1. The running tub was let for 30 minutes to saturation. On the plate also SIN 1C reference solution was dropwise added. On the dropping spot the plate was dried in a cold air flow protected from light and it was let to run up to a 15 cm height. During the running period the running tub was put on a dark place. After evaporation of the solvent the plate was evaluated visually in UV light at 254 nm. SIN 1 presents at 0,05 $R_f$ and SIN 1C at 0.36 $R_f$. We experienced in every case that in the solutions containing CDPSI the intensity of the SIN 1C spot is visibly smaller than in aqueous solutions.

As the transformation of SIN 1 to an inactive metabolite is considerably pH dependent, the measurements were carried out in phosphate buffers of pH 6.4, 7.0 and 7.6 according to the pharmacopoea. In ever case the buffer and 20 mg/ml CDPSI containing buffer solutions were compared, all of them by UV spectophotometric measurement after suitable aqueous-alcoholic dilution, examining the intensity of the SIN 1 decomposition product by thinlayer chromatography.

The results of the spectrophotometric measurement are summarized in Table I.

TABLE I

The change of the λ max. value as function of time (1 mg/ml SIN 1 + 20 mg/ml CDPSI)

| time | λ max. | | | | | |
|---|---|---|---|---|---|---|
| | pH 6.4 | | pH 7.0 | | pH 7.6 | |
| (days) | buffer | +CDPSI | buffer | +CDPSI | buffer | +CDPSI |
| at preparation | | | | | | |
| 0 | 291.5 | 291.9 | 290.6 | 291.0 | 291.2 | 290.9 |
| 1 | 289.0 | 290.5 | 280.4 | 285.5 | 276.4 | 278.8 |
| 4 | 284.9 | 288.5 | — | — | — | — |
| 6 | 279.8 | 283.9 | 277.3 | 278.8 | 277.6 | 277.9 |

The decrease of the maximum UV wavelength of about 13 nm (from 291 nm to 278 nm) represents the total decomposition of SIN 1 to SIN 1C.

In the buffer of pH 6,4 in the presence of CDPSI still after 6 days the Δλ was =7 nm by contrast to the control Δλ=12 nm value. The reproductibility of the UV maximum under the given circumstances was within ±0.5 nm, thus the difference can be considered as significant. After 1 day of storage the Δλ difference could be still measured, by contrast at pH 7.6 the stabilization effect of CDPSI scarcely is discerned.

In the tested solutions the SIN 1: CDPSI molar ratio was about 1:2, which is the necessary minimum for the complexation in solution. The stabilizing effect in solution of the 10 fold excess (10 mg/ml), -corresponding to a complex of 1:1 molar ratio—of CDPSI was scarcely present. The decomposition degree could be followed by thin-layer chromatography too. The SIN 1C spot intensity presented at 0.36 $R_f$ in a pH 6.4 buffer differed still after 1 week of storage noticeably; in a 7 and 7.6 buffer after 1 day of storage a perceptible difference was shown in the intensity of the SIN 1 spot at 0.04 $R_f$. In the pH 7 buffer the unchanged SIN 1 was still perceptible, in that of 7.6 it was practically no longer detectable.

In solution the equilibrium of the dissociation of the complex can be shifted, using the cyclodextrin in an excess. With an extremely great CDPSI excess (1000, 2000 fold respectively) the injectable composition has shown only a spectrum shift of Δλ±1 nm in distilled water after 1 week, while the control solution was practically decomposed.

The quantitive measurement of the decomposition degree was carried out by the HPLC method too.

HPPLC measurement circumstances to the separation of SIN 1-SIN 1 C

| Equipment: | Beckman 114 M Solvent Delivery Module, 165 Variable Wavelength Detektor, Hewlett-Packard 3396 A integrator. |
|---|---|
| Column: | Ultrasphere ODS analytical column 4.6 × 150 nm, 5μ. |
| Eluent: | 0.05 M sodium acetate: 700 ml |
| | acetonitrile: 300 ml |
| | tetrahydrofuran: 2 ml |
| | flowing rate: 1.0 ml/min. |
| | pressure: 120 bar |
| | measuring wavelength: 278, 290 nm |
| | sample volume: 20 μl |
| | sensibility: 0.1 AU |
| | chart speed: 0.5 cm/min. |
| | retention times: $t_R$ SIN1: 2.9 min. |
| | $t_R$ SIN 1C: 4.2 min. |

Results:
1. Solutions of 0.5 mg/ml SIN 1 prepared in phosphate buffer of 6.3 pH protected from light were stored at room temperature. Complex was formed with 50 mg/ml (100 fold quantity) of CDPSI. After storage of 5 weeks the HPLC chromatograms were evaluated.

| Active ingredient content: | Evaluation: | |
|---|---|---|
| | control[x] | CDPSI-complex |
| SIN 1 | 0,016 | 0,17 |
| SIN 1C | 0,23 | 0,16 |

[x]Note: The data of the control measurement relates to distilled water and not to buffer.
CDPSI applied in a 100 fold weight excess (about in a molar ratio of 10:1) is hinders significantly the SIN 1 decomposition. The result obtained is in accordance with the thin-layer-chromatography test.

2. The test was carried out in a pH 7 phosphate buffer too, choosing similar concentration circumstances. (0,5 mg/ml SIN 1 50 mg/ml CDPSI).

The chromatograms obtained after 4 days storage were evaluated.

| Active ingredient content mg/ml | Evaluation: | |
|---|---|---|
| | control | CDPSI-complex |
| SIN 1 | 0.041 | 0.23 |
| SIN 1C | 0.125 | 0.064 | pH value of the solutions after storage:
Control: 6.57
CDPSI: 6.2

It can be considered as proved, that in the concentration used CDPSI hinders even at pH 7 the transformation of SIN 1 to SIN 1C which is an inactive metabolite.

We tested further the stability of SIN 1 injection in a dilute aqueous solution.

From the lyophilized SIN 1 powder ampoule an aqueous solution of 50 µg/ml concentration was prepared, thereafter 20 mg/ml of CDPSI were added. The solutions were stored at room temperature, and from time to time the SIN 1C decomposition product quantity was determined.

The chromatograms obtained after the 1.; 4. and 11. days were evaluated.

| | Evaluation: | |
|---|---|---|
| | SIN 1C content µg/ml | |
| time (days) | control | CDPSI-complex |
| starting | 0.1 | 0.1 |
| 1 day | 0.8 | 0.6 |
| 4 days | 3.9 | 0.94 |
| 11 days | 5.6 | 1.8 |

Thus object of the present invention is a SIN 1 cyclodextrin derivative and the preparation thereof, which is stable in an aqueous system even at physiological pH and in which the transformation to a SIN 1C inactive metabolite is hindered by the applied cyclodextrin derivative.

Surprisingly it was found that with cyclodextrins, especially with CDPSI complexed SIN 1 contains a considerable amount of SIN 1A intermediate after the complex preparation. The transformation process of SIN 1→SIN 1A→SIN 1C in the presence of cyclodextrins was also examined in 0.02M acetate buffer at pH 5.5. Surprisingly the effect of $\beta$-CO was the most pronounced, more than 7 fold more SIN 1A was found in the presence of $\beta$-CO than in the control. (The SIN 1A was detected by HPLC)

Testing the biological effect of the compositions according to the invention in vivo, we found that till SIN-1 used p.o. in a dose of 1 mg/kg does not exert an activity (cardioprotective activity on rats is 11%), the cardioprotective activity of SIN-1-CDPSI applied p.o. with the same active ingredient is 42,2%.

The good biological effectiveness of SIN 1—CDPSI complex in the cardioprotective test after oral administration can be attributed to SIN 1A present in the solid complex. The "A" form which plays a key role in the biological effect, cannot be formed under the pH of gastric medium; it can be generated in-vitro from SIN 1 substance by incubation under below alkaline pH. Upon dissolving the CDPSI complex in distilled water considerable amount of SIN 1A can be detected in the aqueous solution.

It seems that the transition of SIN 1-SIN 1A is promoted by cyclodextrins, and simultaneously the very unstable, oxygen sensitive SIN 1A is stabilized by complexation, which results in slower SIN 1A→SIN 1C transformation. Thus the smoother onset and the longer duration of action are due to a delayed release of nitric oxide from complexed SIN 1.

The following TABLE shows the SIN 1A content of SIN 1 complexes with different cyclodextrins prepared according to Example 2 measured right after the preparation by HPLC. SIN 1 physical mixture at the same composition prepared in the same manner with lactose was used as reference.

TABLE

| (Sample) Complex | SIN 1A content % (given in SIN 1C equivalent) |
|---|---|
| SIN 1 - CDPSI | 1.27 |
| SIN 1 - $\beta$-CO | 0.08 |
| SIN 1 - DIMEB | 0.06 |
| SIN 1 - HP$\beta$CO | 0:115 |
| SIN 1 - lactose reference | — |

Results and conclusions

The relaxing effects of the SIN 1-cyclodextrin complexes and of normal SIN 1 were studied in the concentration 1 or 2 µM.

All four complexes relaxed the sustained contraction of potassium depolarized strips with a maximal effect of 43% to 53%. SIN 1 (1 µM) was somewhat more effective with a relaxation of 58%.

Maximal relaxation occurred with the SIN 1 complexes 23 min to 32 min after administration whereas T/max of SIN 1 was at 18 min. This difference was statistically significant. The duration of action as measured by T/2 was longer with the cyclodextrin-complexes (62 min to 88 min) than with SIN 1 (47 min). This difference was also statistically significant. Thus, the SIN 1-cyclodextrin-complexes showed a smoother onset and a longer duration of action than normal SIN 1.

Since the relaxing effect of SIN 1 is thought to be due to nitric oxide released by an oxidative decomposition process it may be concluded that the complexation of SIN 1 with cyclodextrins slows down this decomposition process. Thus, the smoother onset and the longer duration of action are likely due to a delayed release of nitric oxide from SIN 1-cyclodextrin-complexes.

According to the facts set forth above the invention within inclusion complexes of 3-morpholino-syndonimine or of its salts or its open ring "A" form tautomer isomers are formed with cyclodextrin derivatives.

As cyclodextrin derivative the inclusion complexes according to the invention contain advantageously an ionic, water-soluble cyclodextrin polymer (CDPSI) (molecular weight <10000), heptakis-2,6-dimethyl-β-cyclodextrin (Dimeb), heptakis-2,3,6-tri-O-methyl-β-cyclodextrin (Trimeb) and β or γ-cyclodextrin.

To the preparation of a solid inclusion complex hydroxypropyl-β-cyclodextrin can be used too.

The inclusion complexes according to the invention are prepared by reacting the 3-morpholino-sydnonimine or its salts, in a solvent medium with a cyclodextrin derivative and if desired the complex is obtained from the solution by dehydratation, or by high energy milling of the 3-morpholino-sydnonimine or its salts and the cyclodextrin derivative.

The complex can be advantageously isolated from the solution by lyophilization, spray-drying, evaporation in vacuum at low temperature and by vacuum drying.

The SIN 1 is dissolved with 1-40 mmoles of CDPSI, or Dimeb in 1-500 ml distilled water calculated for 1 mmole of active ingredient, thereafter the dehydration is carried out as mentioned before. The molar ratio of CDPSI polymer is calculated on β-CO. Thus applying the polymer of about 50% β-CO content and of the average 3500 molecular mass the composition of the complex of 1:1 ratio corresponds to about 8%, and and that of 2:1 molar ratio to about 4.5%.

Complex interaction in solution was illustrated by the membrane permeation test

Visking type cellophane membrane (average pore diameter 24 Angstroms) was used. Aqueous solution of SIN 1 at a concentration of 1 mg/ml were put in the donor cell, while distilled water was placed in the receptor compartment of the membrane permeation cell apparatus. The solutions were stirred by magnetic stirrers and were kept at 37°±1° C. At appropriate time intervals samples were taken from the receptor solution and concentration of SIN 1 had permeated from the donor cell was measured by UV-spectrophotometry. The test was repeated in the presence of different cyclodextrins at different concentrations in the donor cell compartment. The time required for the diffusion of 50% SIN 1 ($T_{50}\%$) in the presence of CDPSI at different concentration are listed in the TABLE.

| Diffusion half life of SIN 1 in the presence of CDPSI | $T_{50\%}$ (hours) |
|---|---|
| SIN 1 alone | 0.9 |
| +CDPSI 25 mg/ml | 3.5 |
| 50 mg/ml | 5.0 |

The inclusion complexes prepared according to the invention can be used to the production of pharmaceutical compositions, combinations respectively for stable injectable, oral or local use.

Doses of the inclusion complexes of this invention may vary with the age, body weight and conditions of the subject, the administration route, the number of administrations or the like, but is in the range of 6 to 800 mg per day, perferably 10 to 400 mg per day.

The retard effect prevails particularly in the case of applying the pharmaceutical composition in the form of one-a-day tablets, microcapsules and ointments exceedingly suitable for percutaneous use, respectively. The pharmaceutical compositions of the invention are prepared in a customary manner. The adjuvants and carriers are those which are usually used in the field of pharmaceutical preparations.

The details of the invention are illustrated below in some examples without limiting the invention to the examples.

EXAMPLES

1. Preparation of the SIN-1-CDPSI complex by lyophilization 15 g of (6.6 mmoles) CDPSI polymer are dissolved in 200 ml of distilled water, thereafter to the solution 1.1 g (5.3 mmoles) of SIN 1-HCl are added. The materials are dissolved almost immediately and a pure, clear solution is obtained, which is instantly frozen and dehydrated by lyophilization, taking care, that in the course of any processes the substance should be exposed to the possible minimal light exposure.

It is e.g. expedient to wrap up the alembic with a black paper while dissolving. The product obtained is very light, it is a loose powder, its active ingredient content determined by a spectrophotometric method is: 6.5±0.5%, corresponding about to a molar ratio of 1:1.

Tests proving the fact of complex formation: the thermogravimetric (TG), differential-scanning colorimetric (DSC) and the Thermal Evolution Analysis (TEA) tests have shown characteristic differences between SIN 1 the physical mixtures of SIN 1-CDPSI and SIN 1-CDPSI complex. From the SIN 1 active agent at a temperature of 60°-110° C. about 8% of an inorganic substance is removed; it is possible that it is water. The decomposition while melting of the substance started at a temperature of 170°-180° C. with an explosive violence and in a very tight temperature interval 70% of the introduced agent is removed from the system.

Between 220° and 230° C. the decomposition slows down, and, up to 350° C. a 87% loss of the mass can be register. To the identification of the non-complexed active ingredient the DSC peak between 190°-200° C. and the 190° C. TEA peak causing even in an argon atmosphere an exotherm enthalpy alteration can be used. The thermic curves of the SIN 1-CDPSI physical mixture prepared immediately before measuring can be considered as resultants of the starting materials.

The curves of the complex show a significant discrepancy from those above, the pointed decomposition peaks of SIN 1 do not represent themselves, which means, that SIN 1 really forms an inclusion complex with CDPSI.

Powder X-ray diffraction pattern

According to SIN 1-CDPSI X-ray diffraction tests, the structure is an amorph one. The characteristic reflection peaks of SIN 1 are disappearing. The amorphons structure of CDPSI is known. The crystallisation degree of SIN 1 treated similarly but without CDPSI is though decreasing, but the transition to a total amorphons structure is not possible only by lyophilization. 2 ~ reflection peaks hinting a slightly crystalline form, characteristic to free (not complexed) SIN 1 can't be found in the complex diagram.

2. Preparation of the SIN 1-CDPSI complex by lyophilization 15 g of CDPSI polymer (6.6 mmoles) (β-CO content 53%, COO⁻ content 4.2%) are dissolved in 200 ml of distilled water. In the solution obtained 0.7 g (3.3 mmoles) of SIN 1 are dissolved, thereafter the solution is processed according to example 1.

Active ingredient content of the product obtained is 4.5±0.2%, corresponding about to a 1:2 molar ratio.

3. Preparation of SIN 1-CDPSI complex with high and controlled SIN 1A content Following the process according to Example 2 the obtained solid product is submitted to a second drying to remove the complex bound water. The product was dried at 60° C. under vacuo for 3 hours. (to a constant weight) Loss on drying: 4.5±0.2%. SIN 1A content was increased about five fold during heating, it increased from 1.08% to 5.1% while the SIN 1A/SIN 1C ratio was also altered favorably. (changed from 10 to 17.) Storing the dried complexes at room temperature protected from light more than 3 months the SIN 1A content and the ratio of SIN 1A/SIN 1C of the sample practically was not changed. In the control (not heat-treated) sample during storage the SIN 1A content is also increased from 1.08% to 1.9%, at the same time the ratio of SIN 1A/SIN 1C decreased (changed from 10 to 3). Preparation of SIN 1-CDPSI complex product with high SIN 1A content and controlled composition is possible by a short term heat-treating of the lyophilized SIN 1-CDPSI complex.

4. Preparation of SIN 1 Dimeb complex:

14 g of Dimeb (10.3 mmoles) (moisture content 2%) are dissolved in 100 ml of distilled water. While stirring the solution 1.03 g (5 mmoles) of SIN 1 are added. The clear solution obtained is processed according to example 1 protected from light. The product is a loose white powder, active ingredient content is 6.5±0.2%, the molar ratio corresponds about to 1:2 SIN 1: Dimeb.

5. Preparation of an ointment for percutaneous use with a SIN 1 content of 10 mg and ointment content of 1/2 g From the SIN 1-Dimeb complex prepared according to example 3 (active ingredient content 6.5%) 151 mg are dissolved in 20 ml of distilled water. To the solution protected from light 50 mg of KLUCHEL-HF (hydroxypropylcellulose) are added while vigorous stirring. Thus a viscous solution, hardly miscible is obtained, it is let to stay at room temperature for one day. Thus a transparent jelly is formed, 2 g of which are containing 10 mg of SIN 1.

6. SIN 1 tablet with 2 mg active ingredient content/tablet 80 mg of SIN 1-CDPSI complex, active ingredient content 2.5%,
40 mg of maize startch,
128 mg of milk sugar
2 mg of magnesiumstearate
total weight of the tablet: 250 mg The tablets are prepared by the method known per se, by direct pressure.

What we claim is:

1. An active inclusion complex of 3-morpholino-sydnonimine or of its pharmaceutically acceptable salt or tautomer isomer formed with a cyclodextrin.

2. Inclusion complex as in claim 1 of 3-morpholino-sydnonimine or of its pharmaceutically acceptable salt or tautomer isomer formed with an ionic water soluble cyclodextrin polymer CDPSI, having a molecular weight <10,000.

3. Inclusion complex as in claim 1 of 3-morpholino-sydnonimine or of its pharmaceutically acceptable salt or tautomer isomer formed with hydroxypropyl-β-cyclodextrin.

4. Inclusion complex as in claim 1 of 3-morpholino-sydnonimine or of its pharmaceutically acceptable salt or tautomer isomer formed with heptakis-2,6-dimethyl-β-cyclodextrin.

5. Inclusion complex as in claim 1 of 3-morpholino-sydnonimine or of its pharmaceutically acceptable salt or tautomer isomer formed with heptakis-2,3,6-tri-0-methyl-β-cyclodextrin.

6. Inclusion complex as in claim 1 of 3-morpholino-sydnonimine or of its pharmaceutically acceptable salt or tautomer isomer formed with β- or γ-cyclodextrin.

7. Process for the preparation of the active inclusion complex of N-nitroso-N-morpholino-amino-acetonitrile or its pharmaceutically acceptable salt formed with a cyclodextrin-derivative, which comprises a) reacting the 3-morpholino-sydnonimine or its pharmaceutically acceptable salt in an aqueous medium with a cyclodextrin derivative and the complex is isolated from the solution by dehydration, or b) high energy milling of the 3-morpholino-sydnonimine or its salt and a cyclodextrin derivative, whereby the complexed 3-morpholino-sydnonimine undergoes a transformation to form the N-nitroso-N-morpholino-amino-acetonitrile.

8. Process according to claim 7, wherein as cyclodextrin derivative an ionic, water soluble cyclodextrin polymer (molecular weight<10.000); hydroxypropyl-cyclodextrin, heptakis-2,6-O-dimethyl-β-cyclodextrin, heptakis-2,3,6-tri-O-methyl-β-cyclodextrin or β-cyclodextrin are used.

9. Pharmaceutical composition, containing as active ingredient a therapeutically effective amount of the inclusion complex of claim 1 or 3-morpholino-sydnonimine or of its pharmaceutically acceptable salt, or tautomer isomer formed with a cyclodextrin together with a pharmaceutically acceptable inert carrier.

10. Pharmaceutical composition according to claim 9, formulated in an oral form.

11. Pharmaceutical composition according to claim 9, which contains as a cyclodextrin an ionic, water soluble polymer CDPSI having a molecular weight<10,000; hydroxypropyl-β-cyclodextrin, heptakis-2,6-O-dimethyl-β-cyclodextrin, heptakis-2,3,6-tri-O-methyl-β-cyclodextrin, β-cyclodextrin or γ-cyclodextrin.

12. Method of treatment of anginic or ischemic disease in a human in need of said treatment which comprises administering to the human a therapeutically effective amount of an active inclusion complex of 3-morpholino-sydnonimine or its pharmaceutically acceptable salt or tautomer thereof formed with a cyclodextrin as defined in claim 1.

13. An active inclusion complex of N-nitroso-N-morpholino-amino-acetonitrile or of its pharmaceutically acceptable salt formed with a cyclodextrin.

14. The inclusion complex defined in claim 13 of N-nitroso-N-morpholino-amino-acetonitrile or of its pharmaceutically acceptable salt with an ionic water-soluble cyclodextrin polymer CDPSI having a molecular weight <10,000.

15. A process for the preparation of an active inclusion complex of N-nitroso-N-morpholino-amino-acetonitrile or of its pharmaceutically acceptable salt formed with a cyclodextrin, which comprises the steps of:

(a) complexing 3-morpholino-sydnonimine or a pharmaceutically acceptable salt thereof with the cyclodextrin in an aqueous medium and isolating by dehydration the cyclodextrin inclusion complex of the 3-morpholino-sydnonimine or the pharmaceutically acceptable salt thereof thus formed as a solid product; and (b) subjecting the cyclodextrin inclusion complex of the 3-morpholino-sydnonimine or the pharmaceutically acceptable salt thereof to a subsequent drying step at 60° C., under vacuum for 3 hours, to remove bound water from said inclusion complex and to form the cyclodextrin inclusion complex of N-nitroso-N-morpholino-amino-acetonitrile or the pharmaceutically acceptable salt thereof.

16. The process defined in claim 15 wherein the cyclodextrin is an ionic, water-soluble cyclodextrin polymer CDPSI having a molecular weight <10,000.

17. The process defined in claim 15 wherein according to step (a) the dehydration of the cyclodextrin inclusion complex of the 3-morpholino-sydnonimine or the pharmaceutically acceptable salt thereof is carried out by lyophilization.

* * * * *

UNITED STATES PATENT AND TRADEMARK OFFICE
CERTIFICATE OF CORRECTION

PATENT NO. : 5,298,496
DATED : March 29, 1994
INVENTOR(S) : Maria Vikmon et al

It is certified that error appears in the above-indentified patent and that said Letters Patent is hereby corrected as shown below:

Col. 2, line 13 for "$A^{1\%}_{1cm} = 1220$" read -- $A^{1\%}_{1cm} = 1220$ --;

Col. 3, line 1, line 13, (3 occurrences) and line 16 (2 occurrences) for "CO" read -- CD --;

Col. 3, line 37, for "dose" read -- does --;

Col. 3, line 60, for "ever" read -- every --;

Col. 5, lines 63 and 65, for "CO" read -- CD --;

UNITED STATES PATENT AND TRADEMARK OFFICE
CERTIFICATE OF CORRECTION

PATENT NO. : 5,298,496
DATED : March 29, 1994
INVENTOR(S) : Maria Vikmon et al

It is certified that error appears in the above-indentified patent and that said Letters Patent is hereby corrected as shown below:

Col. 6, in the Table, lines 33 and 35, for "CO" read -- CD--;

Col. 7, lines 23 and 24, for "CO" read -- CD --;

Col. 8, line 60, for "~" read -- θ --;

Col. 8, line 66, for "CO" read -- CD -- ;

Col. 9, line 38, for "1/2 g" read -- 2g --; and

Col. 9, line 41, for "151mg" read --1510 g --.

Signed and Sealed this

Eighteenth Day of July, 1995

Attest:

BRUCE LEHMAN

*Attesting Officer*     Commissioner of Patents and Trademarks